United States Patent
Edwards et al.

(10) Patent No.: US 7,116,103 B2
(45) Date of Patent: Oct. 3, 2006

(54) NUCLEAR MAGNETIC RESONANCE METHOD AND APPARATUS FOR EVALUATING A CHARACTERISTIC OF A REGION

(75) Inventors: Carl M. Edwards, Katy, TX (US); Daniel T. Georgi, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 17 days.

(21) Appl. No.: 10/967,733

(22) Filed: Oct. 18, 2004

(65) Prior Publication Data

US 2006/0082367 A1    Apr. 20, 2006

(51) Int. Cl.
*G01V 3/00* (2006.01)

(52) U.S. Cl. .................. 324/303; 324/300

(58) Field of Classification Search ........ 324/303, 324/300, 309, 307, 306, 318, 322
See application file for complete search history.

(56) References Cited

U.S. PATENT DOCUMENTS

| | | | | |
|---|---|---|---|---|
| 4,734,646 | A | * | 3/1988 | Shenoy et al. ............ 324/309 |
| 5,153,514 | A | * | 10/1992 | Griffin et al. ............ 324/303 |
| 6,023,163 | A | * | 2/2000 | Flaum et al. ............ 324/303 |
| 6,097,184 | A | * | 8/2000 | Flaum ............ 324/303 |
| 6,570,382 | B1 | * | 5/2003 | Hurlimann et al. ......... 324/303 |
| 6,580,272 | B1 | | 6/2003 | Freed et al. ............ 324/303 |
| 6,891,369 | B1 | * | 5/2005 | Hurlimann et al. ......... 324/303 |
| 2003/0178994 | A1 | | 9/2003 | Hurlimann et al. ......... 324/303 |
| 2005/0162162 | A1 | * | 7/2005 | Itskovich et al. ........... 324/303 |

OTHER PUBLICATIONS

D.E. Freed, M.D. Hurlimann, and U.M. Scheven; "The Equivalence Between Off-Resonance and On-Resonance Pulse Sequences and Its Application to Steady-State Free Precession with Diffusion in Inhomogeneous Fields," Journal of Magnetic Resonance 162; 2003; pp. 328-335.
D.E. Freed, U.M. Scheven, L.J. Zielinski, P.N. Sen, and M.D. Hurlimann; "Steady-state Free Precession Experiments and Exact Treatment of Diffusion in a Uniform Gradient," Journal of Chemical Physics, vol. 115, No. 9; Sep. 2001; pp. 4249-4258.
M.D. Hurlimann, L. Venkataramanan, C. Flaum, P. Speier, C. Karmonik, R. Freedman, and N. Heaton; "Diffusion-Editing: New NMR Measurement of Saturation and Pore Geometry;" SPWLA 43rd Annual Logging Symposium, Jun. 2-5, 2002; pp. 1-14.
International Search Report for International application No. PCT/US05/36882. Mailed Jan. 27, 2006.

* cited by examiner

*Primary Examiner*—Brij B. Shrivastav
(74) *Attorney, Agent, or Firm*—Cantor Colburn LLP

(57) ABSTRACT

A method of evaluating a characteristic of a fluid in a region, and a nuclear magnetic resonance (NMR) well logging apparatus for the implementation thereof, is disclosed. A magnetic field gradient is applied to the region, and first and second sequences of magnetic field gradient is applied to the region, with the second sequence differing in a pulse characteristic from the first sequence. A magnetization spectrum resulting from each of the sequences of pulse is captured, and a change in the magnetization spectrum resulting from the first and second sequences of pulses is analyzed to extract information about the fluid.

27 Claims, 5 Drawing Sheets

NUCLEAR MAGNETIC RESONANCE METHOD AND APPARATUS FOR EVALUATING A CHARACTERISTIC OF A REGION

BACKGROUND OF THE INVENTION

The present disclosure relates generally to a nuclear magnetic resonance (NMR) method and apparatus for evaluating a characteristic of a region, and particularly for evaluating a characteristic of a fluid in a subterranean region.

NMR oil well logging is a technique used to investigate subterranean regions that may contain oil reserves. The nuclei of chemical elements have a characteristic angular momentum (spin) and a magnetic moment, and by detecting and analyzing the reaction of the nuclei to applied magnetic fields, the characteristics of specific nuclei may be deduced. In the presence of an externally applied static magnetic field ($B_0$), the nuclei spins become magnetized and align themselves parallel to the $B_0$ field. By applying a radio frequency (RF) pulse train of a specific frequency to the magnetized nuclei, a pulsed RF magnetic field ($B_1$) is generated that tips, or flips, the spins away from the direction of the $B_0$ field. If the RF frequency ($\omega$) matches the condition for NMR ($\omega=\gamma B_0$), where $\gamma$ is the gyromagnetic ratio, then the first pulse reorients the magnetization to start precession and subsequent pulses generate spin-echo signals. A RF pulse sequence known as the CPMG (Carr-Purcell-Meiboom-Gill) sequence is typically used for oil well logging.

At the end of a ninety degree tipping pulse, the spins are oriented transverse to the $B_0$ field and precess around the direction of the $B_0$ field at the Larmor frequency ($\omega_0=\gamma B_0$), and the transverse magnetization dephases with a transverse relaxation time constant ($T_2$), also known as the spin-spin relaxation time. Repeated tipping and relaxation of the spins results in the NMR spin-echo signal, which may then be detected and analyzed for oilfield exploration. However, heavy oil is difficult to discriminate from bound water using conventional NMR well logging contrasting techniques because their relaxation times are similar. Even though the diffusion constant of heavy oils is at least ten times smaller than that of water, changes in $T_2$ are small for typical logging echo times. Accordingly, there is a need in the art for a NMR detection and analysis method that overcomes these drawbacks.

SUMMARY OF THE INVENTION

Embodiments of the invention include a method of evaluating a characteristic of a fluid in a region. A magnetic field gradient is applied to the region, and first and second sequences of magnetic field pulses are applied to the region, with the second sequence differing in a pulse characteristic from the first sequence. A magnetization spectrum resulting from each of the sequences of pulses is captured, and a change in the magnetization spectrum resulting from the first and second sequences of pulses is analyzed to extract information about the fluid.

Other embodiments of the invention include another method of evaluating a characteristic of a fluid in a region. A magnetic field gradient is applied to the region, and first and second sequences of magnetic field pulses are applied to the region, where each of the sequences having a power spectrum with an energy distribution across a range of frequencies in a series of closely spaced sticks, and where the second sequence differs in pulse characteristic to the first sequence. A resultant magnetization spectrum is analyzed to extract information relating to signal attenuation resulting from the characteristics of the fluid in the region.

Further embodiments of the invention include a nuclear magnetic resonance (NMR) well logging apparatus having a field gradient generator, a signal generator, a signal receiver, and a processing circuit. The field gradient generator is operational to apply a static magnetic field gradient to a fluid of a subterranean region. The signal generator is operational to apply first and second sequences of magnetic pulses to the region, and the signal receiver is operational to receive a NMR signal responsive to the pulses. The processing circuit is coupled with the signal generator and the signal receiver, the processing circuit being programmed with instructions which, when executed by the processing circuit cause the signal generator to generate first and second sequences of magnetic field pulses to the region, the signal receiver to receive a resultant NMR signal from the region, and cause the processing circuit to capture a magnetization spectrum in response to each of the first and second sequences of magnetic field pulses, and analyze a change in the magnetization spectrum resulting from the first and second sequences and extract therefrom information about the fluid.

Yet further embodiments of the invention include a nuclear magnetic resonance (NMR) well logging apparatus having a field gradient generator, a signal generator, a signal receiver, a processing circuit, and a storage medium. The field gradient generator is configured to apply a static magnetic field gradient to a fluid of a subterranean region. The signal generator is configured to apply first and second sequences of magnetic pulses to the region. The signal receiver is configured to receive information responsive to the pulses, and the processing circuit is configured to control the pulses and to analyze the received information. The storage medium, readable by the processing circuit, stores instructions for execution by the processing circuit for applying first and second sequences of magnetic field pulses to the region, capturing a magnetization spectrum resulting from each of the sequences of pulses, and analyzing a change in the magnetization spectrum resulting from the first and second sequences of pulses to extract information about the fluid.

BRIEF DESCRIPTION OF THE DRAWINGS

Referring to the exemplary drawings wherein like elements are numbered alike in the accompanying Figures.

DETAILED DESCRIPTION OF THE INVENTION

Embodiments of the invention provide a nuclear magnetic resonance (NMR) well logging method and apparatus for applying a sequence of magnetic field pulses having a power spectrum to a fluid of a subterranean region so as to magnetically excite the region in such a manner that results in a magnetization spectrum having a signal amplitude and attenuation characteristic representative of the composition of the fluid in the region. By using steady-state free precession (SSFP) methods in combination with known differences between the diffusion constants of oil and water in a NMR well logging apparatus, it is possible to identify the presence of oil in a subterranean region, and to distinguish between heavy oil and bound water. While embodiments described herein depict oil and water as exemplary fluids, it will be appreciated that the disclosed invention may also be applicable to other fluids having identifiable material characteristics as herein disclosed.

Figure 1:
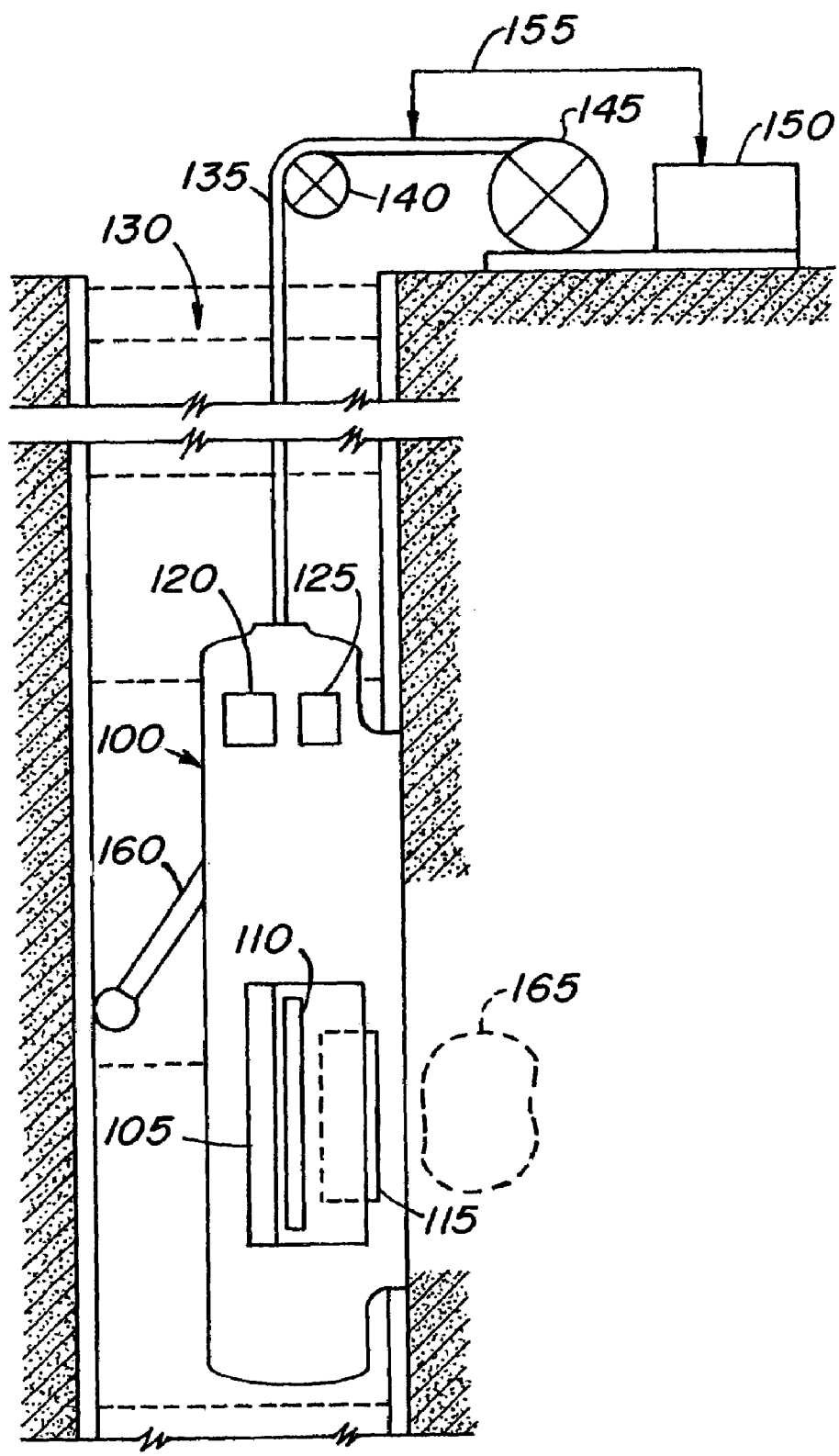
FIG. 1 depicts an exemplary nuclear magnetic resonance (NMR) well logging apparatus for use in accordance with embodiments of the invention.

FIG. 1 is an exemplary embodiment of a nuclear magnetic resonance (NMR) well logging apparatus 100 having a field gradient generator 105, a signal generator 110, a signal receiver 115, a processing circuit 120, and a storage medium 125. In an exemplary application, logging apparatus 100 is suspended in a borehole 130 via a cable 135, a pulley 140, a drivewheel 145, and surface equipment 150, which controls the lowering and raising action of cable 135 as represented by control line 155. Apparatus 100 may be pressed against one side of borehole 130 via a control arm 160. Field gradient generator 105 is configured to apply a static magnetic field gradient G to a fluid of a subterranean region, generally represented at 165. Signal generator 110 is configured to apply a sequence of magnetic pulses to region 165, and signal receiver 115 is configured to receive information, and specifically nuclear magnetic resonance information, in response to the pulses from signal generator 110. The pulses from signal generator 110 and the information received at signal receiver 115 are controlled and analyzed by processing circuit 120. Storage medium 125, readable by processing circuit 120, stores instructions for execution by processing circuit 120 for performing method embodiments of the invention, which will now be discussed in more detail.

Figure 2:
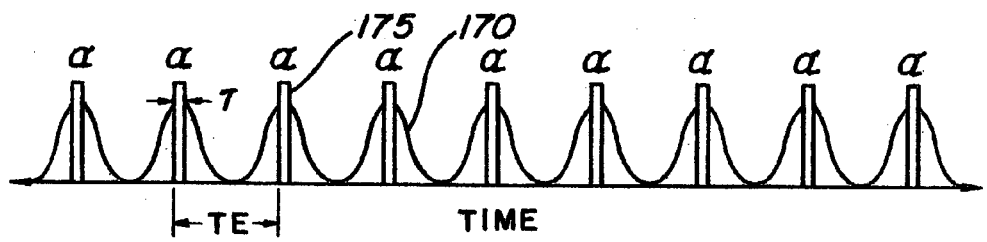
FIG. 2 depicts an exemplary sequence of magnetic field pulses and a resultant steady-state free precession (SSFP) signal for use with the apparatus of FIG. 1.

Referring now to FIG. 2, a steady-state free precession (SSFP) signal 170 is depicted that results from an applied sequence of magnetic field pulses (e.g. RF pulses) 175 provided by signal generator 110 and directed toward region 165. As a general matter, SSFP is the name given in the art of NMR to the NMR phenomena that occurs during a long series of equally spaced identical pulses long after any transients have decayed, which is the situation illustrated by FIG. 2. In an embodiment, the sequence of pulses 175 is a Carr-Purcell-Meiboom-Gill (CPMG) sequence. However, embodiments of the invention are not limited to CPMG sequences and may be applicable to other repetitive pulse sequences. Pulses 175 have a width $\tau$, a flip angle $\alpha$, and a leading edge spacing TE, all depicted with respect to time. The resulting SSFP signal 170 is sensitive to flip angle $\alpha$, spacing TE, and the diffusion constant D of the fluid in region 165, which will be discussed in more detail later.

In response to magnetic field gradient G, provided by field gradient generator 105 and directed toward region 165, the spins of the nuclei of the fluid in region 165 align themselves along the direction of the static field, and in response to the sequence of pulses 175, the spins of the nuclei are tipped through flip angle $\alpha$. If pulses 175 have flip angles $\alpha$ that are less than 180-degrees, the transverse and longitudinal magnetization components will be mixed and the longitudinal magnetization will have a steady-state condition that is different from the equilibrium condition.

Figure 3:
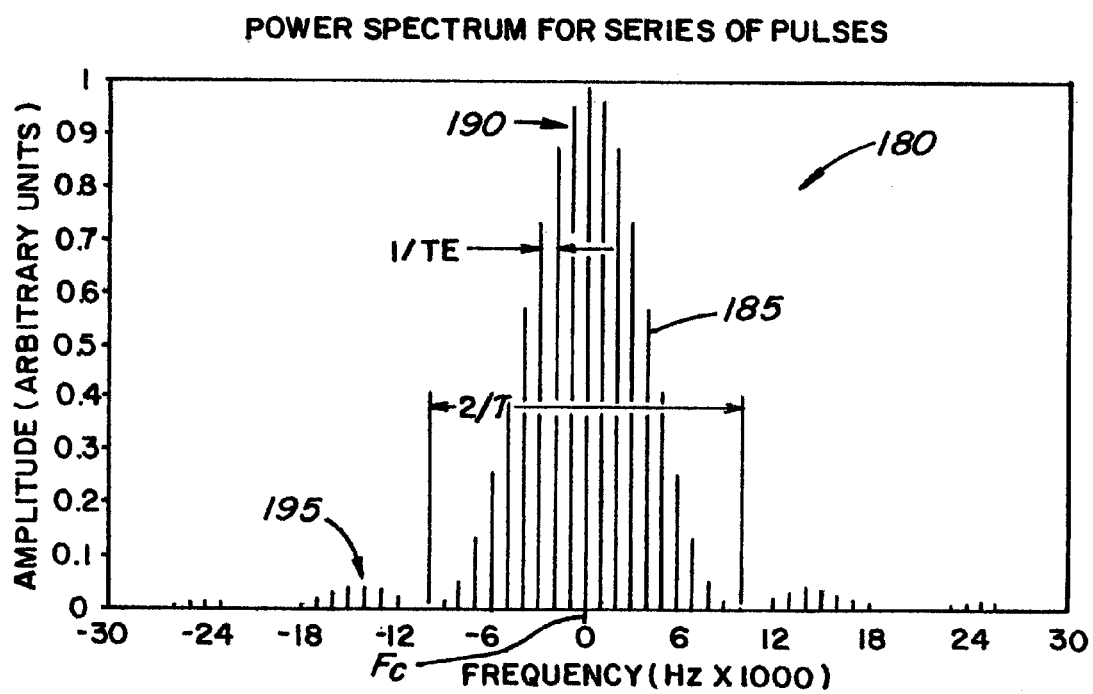
FIG. 3 depicts an exemplary power spectrum associated with the steady stream of pulses of FIG. 2.

A representative power spectrum 180 associated with the steady stream of pulses 175 of FIG. 2 is illustrated in FIG. 3. Power spectrum 180 is described as a stick spectrum having an energy distribution defined by closely spaced sticks, or bands, 185 defining a stick spectra, spaced 1/TE apart in frequency and distributed across a range of frequencies centered about a central characteristic frequency Fc. Characteristic frequency Fc is depicted in FIG. 3 as being normalized to 0-Hertz. The amplitude of the stick spectra of power spectrum 180 are modulated by the square of the Fourier transform of a single pulse 175 and normalized to the amplitude of the stick spectra at characteristic frequency Fc. Power spectrum 180 has a central peak 190 and non-central peaks 195, with central peak 190 having a width of $2/\tau$ in frequency. The width of the stick spectra is given by the inverse train length.

Figure 4:
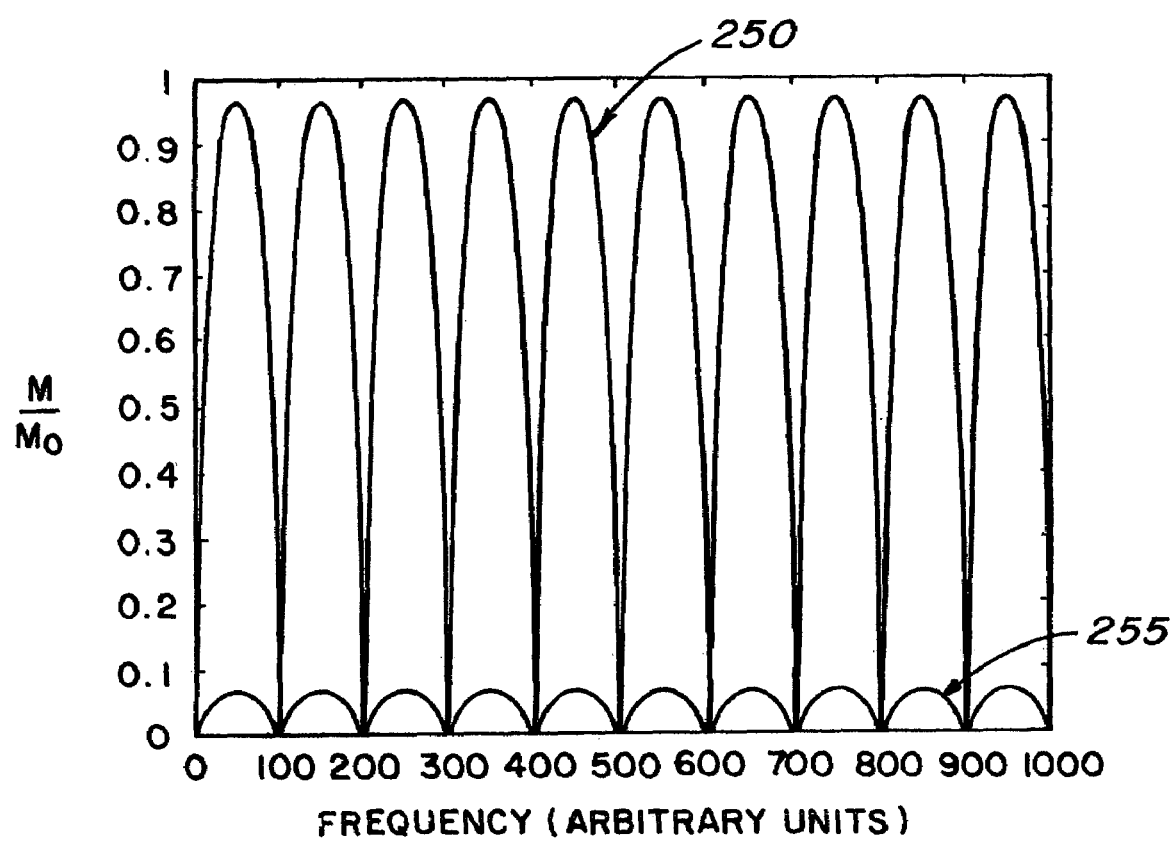
FIG. 4 depicts an exemplary resultant magnetization spectrum in accordance with embodiments of the invention.

In response to power spectrum 180 being received at region 165 during an oil well logging procedure, a periodic magnetization spectrum in the longitudinal magnetization results. Representative magnetization spectrum 250, 255 for oil and water, respectively, are depicted in FIG. 4, which will be discussed in more detail later. By repeating the CPMG sequence with changes in flip angle $\alpha$ and echo time TE, the magnetization spectrum may exhibit different amplitudes, exemplified by 250 and 255 in FIG. 4, and by analyzing the amplitude variations, information about the fluid, and particularly about the oil, in region 165 may be obtained.

During logging, the excited region ($r_0$) of region 165 is centered about the location where the Larmor frequency of the spins matches the frequency of the applied RF 175, such that $$\gamma B(r_0) = \omega_{RF}.$$

Expanding the magnetic field about $r_0$ to the first order results in $$B = B_0 + G \cdot (r - r_0).$$

Thus, the Larmor frequency of the spins in the excited region is proportional to the distance along the direction of the gradient. When a series of pulses exemplified by FIG. 2 are applied, the frequency of the sticks 185 in the power spectrum coincide with discreet locations in the excited region, such that $$\omega_{stick} - \omega_{RF} = \gamma G \Delta z,$$

where $\Delta z$ is the distance along the direction of the gradient from the center of the excited region, as previously indicated. In an embodiment, the characteristics $\tau$, $\alpha$ and TE that define the sequence of pulses 175 are selected such that region 165 is magnetically excited essentially only at the frequencies of the stick spectra 185. As a result of spin-spin relaxation of the magnetically excited nuclei in region 165, a resultant magnetization stick spectra may be broader in the NMR spectrum (magnetization spectrum) 250, 255 than they are in the pulse power spectrum 180, with the magnetization stick spectra of the respective magnetization spectrum 250, 255 having a width of about $1/T_2$, where $T_2$ is the spin-spin relaxation time of the fluid in region 165. In the absence of diffusion, that is, in the absence of a fluid in region 165 having a relatively high diffusion constant D, the resultant NMR spectrum will show signal attenuation only in the neighborhood of its associated stick spectra. In the presence of diffusion, that is, in the presence of a fluid in region 165 having a relatively high diffusion constant D, the resultant NMR spectrum will show attenuation of some of the signal between its associated stick spectra, which results in attenuation of the magnetization signal overall.

FIG. 4 depicts resultant NMR spectrum 250, 255 for oil and water, respectively, and more specifically depicts resultant equilibrium longitudinal magnetization as a function of frequency. The difference between spectrum 250 and spectrum 255 is caused by diffusion, with the oil magnetization spectrum 250 being substantially equal to unity across the frequency range, and the water magnetization spectrum 255 being substantially less than unity across the frequency range. By analyzing the integral of the resultant magnetization spectrum as a function of frequency, logging tool 100 can sense the difference between oil and water in region 165.

In a series of pulses 175 where τ is small, the resulting stick spectra 185 will be far apart, and the resultant NMR signal attenuation as a result of diffusion will be minimal and independent of the diffusion constant D of the fluid in region 165. In a series of pulses 175 where TE is large, the resulting stick spectra 185 will be close together, and the resultant NMR signal attenuation as a result of diffusion will be dependent upon the diffusion constant D of the fluid in region 165. As a result of the relationship between signal attenuation and diffusion constant D, a cutoff value for TE may be defined by $$\frac{1}{TE} \leq \gamma G \sqrt{2DTE}. \qquad \text{Equation-1}$$

Here, γ represents a magnetogyric ratio, which is a fundamental nuclear constant that has a different value for the nucleus of every chemical element. Equation-1 illustrates a condition where the spacing 1/TE of the stick spectra 185 must be less than a threshold rms (root mean square) frequency for a fluid molecule to diffuse in the time TE between pulses 175.

Rearranging Equation-1 yields, $$TE^{3/2} \geq \frac{1}{\gamma G \sqrt{2D}}, \qquad \text{Equation-2}$$

which if met, illustrates a condition where the whole resultant NMR spectrum will be attenuated instead of just being attenuated in the neighborhood of the frequencies associated with its stick spectra.

By applying values for γ and D that relate to water and applying the appropriate selection of pulse width τ and time TE between pulses 175, the sequence of pulses 175 may be tuned to maximize the signal attenuation of magnetization spectrum 250, 255 in the presence of water in region 165, thereby resulting in a magnetization spectrum 255 for water being more attenuated than a magnetization spectrum 250 for oil. Using a differential attenuation analysis method, it may be possible to distinguish between the presence of oil and water in subterranean region 165, since heavy oils have at least a tenfold smaller diffusion constant than water. The relationship between the diffusion constants of oil and water is represented by the following $$(D_O)^{-1/2} \geq \gamma G (\sqrt{2TE})^3 \geq (D_W)^{-1/2}, \qquad \text{Equation-3}$$

where $D_O$ represents a diffusion constant for oil and $D_W$ represents a diffusion constant for water. By analyzing the resultant magnetization spectrum 250, 255 at the frequencies associated with its stick spectra, the degree of signal attenuation may be identified. With the selection of appropriate parameters for the sequence of pulses 175, as discussed previously, the presence of a magnetization signal at frequencies only in the neighborhood of its stick spectra will correlate with the absence of diffusion in the fluid in region 165, indicative of the presence of oil, and the presence of a magnetization signal at frequencies between its stick spectra will correlate with the presence of diffusion in the fluid in region 165, indicative of the presence of water.

The calibration or tuning of the aforementioned differential attenuation analysis method may be accomplished by using an appropriate sequence of pulses 175 that would saturate the nuclei magnetization of the fluid in region 165 at only the frequencies of the stick spectra 185 if the region contained essentially only water. Such tuning would yield a condition where the magnetization signal from region 165 containing essentially only water would be entirely saturated, while the magnetization signal from region 165 containing oil would only be partially saturated, thereby accentuating signal attenuation in the presence of water.

Figure 5:
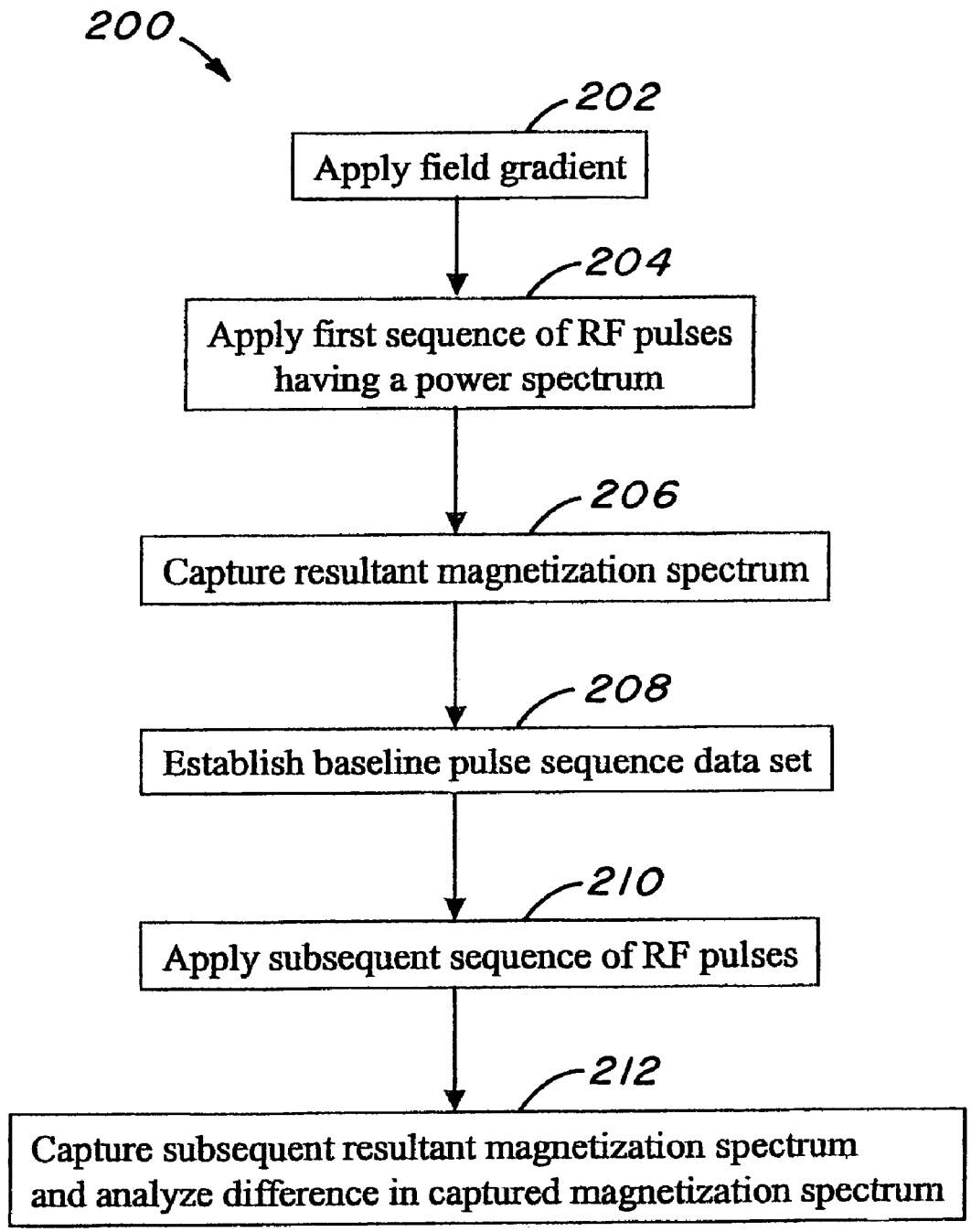
FIG. 5 depicts an exemplary method in accordance with embodiments of the invention.

In view of the foregoing, and with reference now to FIG. 5, it will be appreciated that a method 200 for evaluating a diffusion characteristic D of a fluid in region 165 may be accomplished by: applying 202 a magnetic field gradient G to region 165; applying 204 a sequence of magnetic field pulses 175, such as a CPMG sequence having a power spectrum 180 for example, to region 165 to set up the SSFP signal 170; capturing 206 a magnetization spectrum 250, 255 resulting from pulses 175 where the associated stick spectra may or may not have been broadened by diffusion; using this as an initial condition to establish 208 a baseline CPMG data set; applying 210 a series of second CPMG sequences with changes in flip angle α and echo time TE to acquire the data attenuated by the first CPMG sequence; and analyzing 212 the amplitude of the magnetization spectrum 250, 255 associated with each of the second CPMG sequences to extract signal attenuation information representative of the diffusion characteristic D of the fluid, and more specifically to produce an estimate of the oil signal.

Figure 6:
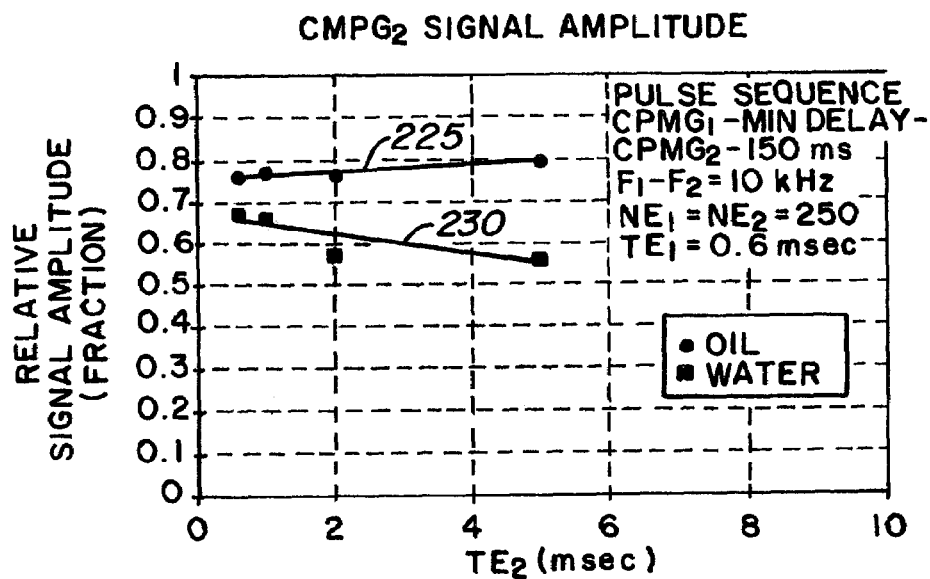
FIG. 6 depicts experimental data obtained using embodiments of the invention.
Figure 7:
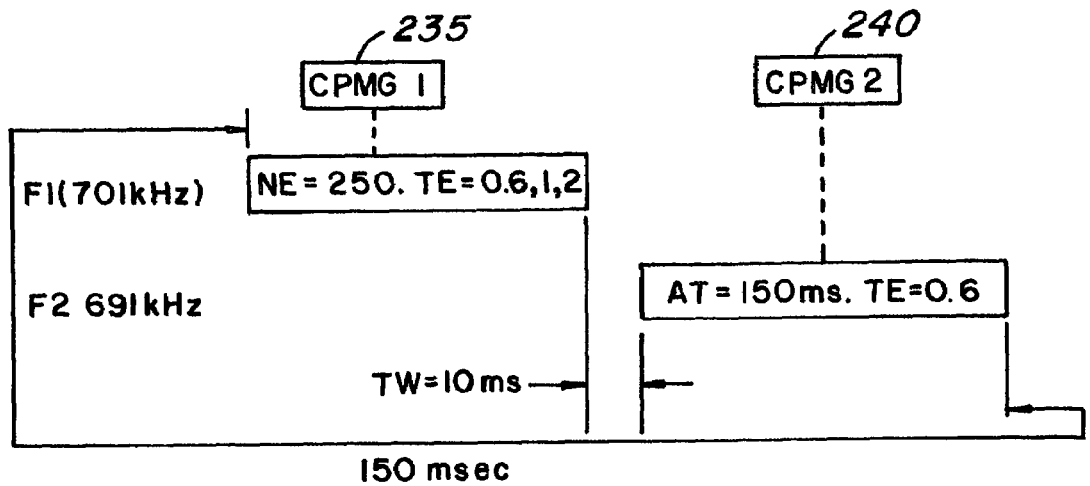
FIG. 7 depicts an arrangement of Carr-Purcell-Meiboom-Gill (CPMG) sequences used to generate the data of FIG. 5.

Experimental data obtained using embodiments of the invention are depicted in FIG. 6, which illustrates second CPMG sequence signal amplitudes for SAE 5W-20 motor oil 225 and water doped with $CuSO_4$ 230 as a function of pulse spacing TE. The mean relaxation time $T_2$ for the motor oil was 46.9 msec (milliseconds), while the mean relaxation time $T_2$ for the doped water was 68.4 msec. The data of FIG. 6 was obtained using two CPMG sequences at two closely spaced frequencies having a frequency difference Δf of 10 kHz (kiloHertz). The frequency of the first signal 235 was 701 kHz, the frequency of the second signal 240 was 691 kHz, the timing between signals was 10 msec, and the wait time between pulse sequences was 150 msec, which is illustrated in FIG. 7. The initial CPMG sequence was used to set up the SSFP signal, and the second to acquire the data attenuated by the first CPMG sequence. The pulse sequences used a first flip angle $\tau_a$ of 90-degrees and a second flip angle $\tau_b$ of 135-degrees. The echo spacing TE for the second CPMG sequence was fixed at 0.6 msec, while the TE for the first CPMG sequence was 0.6, 1, 2 and 5 msec.

The resultant data illustrated in FIG. 6 represents the magnetization spectrum signal amplitudes associated with the second CPMG sequences as a function of the echo spacing TE in the first CPMG sequence. As depicted, the signal amplitude from the oil sample 225 remains substantially constant with increasing TE, while the signal amplitude from the water sample 230 decreases with increasing TE. As illustrated, it has been observed that the distinction between the oil and water signals 225, 230 may be accomplished for a pulse spacing TE equal to or less than about 8 msec.

As discussed previously, an embodiment of apparatus 100 may include processing circuit 120 and storage medium 125, where storage medium 125 is readable by processing circuit 120 and stores instructions for execution by processing circuit 120 for performing the analysis 220 according to the previously discussed methods. However, it will be appreciated that the processing of the data logged by apparatus 100 may or may not occur locally. For example, an embodiment of the invention may include a local storage medium 125 at apparatus 100, but a remote processing circuit 120 at surface equipment 150. Another embodiment of the invention my include a remote storage medium 125 and a remote processing circuit 120 at surface equipment 150, with a communication link via a hardwire (not shown) running alongside cable 135, or via a wireless communication scheme. Accordingly, embodiments of the invention are not limited to local processing of the acquired data.

In view of the foregoing, embodiments of the invention may be embodied in the form of computer-implemented processes and apparatuses for practicing those processes. Other embodiments of the invention may be embodied in the form of computer program code containing instructions embodied in tangible media, such as floppy diskettes, CD-ROMs, hard drives, or any other computer readable storage medium, wherein, when the computer program code is loaded into and executed by a computer, the computer becomes an apparatus for practicing the invention. Further embodiments of the invention may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. Where implemented on a general-purpose microprocessor, the computer program code segments configure the microprocessor to create specific logic circuits. The technical effect of the executable instructions is to analyze a NMR signal, and particularly to analyze a magnetization spectrum of a NMR signal, to evaluate a characteristic of a fluid in a subterranean region, and specifically to distinguish between the presence of oil or water in the region.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A nuclear magnetic resonance (NMR) well logging apparatus, comprising:
    a field gradient generator operational to apply a static magnetic field gradient to a fluid of a subterranean region;
    a signal generator operational to apply first and second sequences of magnetic pulses to the region;
    a signal receiver operational to receive a NMR signal responsive to the pulses;
    a processing circuit coupled with the signal generator and the signal receiver, the processing circuit being programmed with instructions which, when executed by the processing circuit:
    cause:
    the signal generator to generate first and second sequences of magnetic field pulses to the region;
    the signal receiver to receive a resultant NMR signal from the region; and
    cause the processing circuit to:
    capture a magnetization spectrum in response to each of the first and second sequences of magnetic field pulses, the magnetization spectrum being represented as a function of frequency; and
    analyze a change in the magnetization spectrum resulting from the first and second sequences and extract therefrom information about the fluid.

2. The apparatus of claim 1, wherein the processing circuit is further programmed with instructions which, when executed by the processing circuit:
    cause the signal generator to:
    apply a sequence of magnetic field pulses having a power spectrum with an energy distribution across a range of frequencies in a series of closely spaced sticks; and
    cause the processing circuit to:
    analyze the captured magnetization spectrum to extract information relating to signal attenuation; and
    analyze the signal attenuation in relation to a diffusion characteristic relating to the fluid.

3. The apparatus of claim 2, wherein the processing circuit is further programmed with instructions which, when executed by the processing circuit:
    cause the signal generator to:
    apply a sequence of magnetic field pulses that magnetically excites the region at substantially only the frequencies of the sticks of the energy distribution of the applied sequence of pulses;
    apply a sequence of magnetic field pulses that saturate the nuclei magnetization of water; and
    apply a sequence of magnetic field pulses having a pulse spacing TE according to the following equation:

$$TE^{3/2} \geq \frac{1}{\gamma G \sqrt{2D}},$$

where γ represents a magnetogyric ratio, G represents a field gradient, and D represents a diffusion constant.

4. A nuclear magnetic resonance (NMR) well logging apparatus, comprising:
    a field gradient generator configured to apply a static magnetic field gradient to a fluid of a subterranean region;

a signal generator configured to apply first and second sequences of magnetic pulses to the region;

a signal receiver configured to receive information responsive to the pulses;

a processing circuit configured to control the pulses and to analyze the received information; and a storage medium, readable by the processing circuit, storing instructions for execution by the processing circuit for:

applying first and second sequences of magnetic field pulses to the region;

capturing a magnetization spectrum resulting from each of the sequences of pulses, the magnetization spectrum being represented as a function of frequency; and analyzing a change in the magnetization spectrum resulting from the first and second sequences of pulses to extract information about the fluid.

5. The apparatus of claim 4, wherein the storage medium further stores instructions for execution by the processing circuit for:

applying a sequence of magnetic field pulses having a power spectrum with an energy distribution across a range of frequencies in a series of closely spaced sticks;

analyzing a resultant magnetization spectrum to extract information relating to signal attenuation; and analyzing the signal attenuation in relation to a diffusion characteristic relating to the fluid.

6. The apparatus of claim 5, wherein the storage medium further stores instructions for execution by the processing circuit for:

magnetically exciting the region at substantially only the frequencies of the sticks of the energy distribution of the applied sequence of pulses;

applying a sequence of magnetic field pulses configured to saturate the nuclei magnetization of water; and applying a sequence of magnetic field pulses having a pulse spacing TE according to the following equation:

$$TE^{3/2} \geq \frac{1}{\gamma G \sqrt{2D}},$$

where $\gamma$ represents a magnetogyric ratio, G represents a field gradient, and D represents a diffusion constant.

7. A method of evaluating a characteristic of a fluid in a region, comprising:

applying a magnetic field gradient to the region;

applying first and second sequences of magnetic field pulses to the region, the second sequence differing in a pulse characteristic from the first sequence;

capturing a magnetization spectrum resulting from each of the sequences of pulses, the magnetization spectrum being represented as a function of frequency; and analyzing a change in the magnetization spectrum resulting from the first and second sequences of pulses to extract information about the fluid.

8. The method of claim 7, wherein the applying first and second sequences of magnetic field pulses comprises:

applying a sequence of equally spaced pulses.

9. The method of claim 7, wherein the applying first and second sequences of magnetic field pulses comprises:

magnetically exciting the region only at defined frequencies relating to the applied sequence of pulses.

10. A method of evaluating a characteristic of a fluid in a region, comprising:

applying a magnetic field gradient to the region;

applying first and second sequences of magnetic field pulses to the region, the second sequence differing in a pulse characteristic from the sequence, wherein the applying first and second sequences of magnetic field pulses comprises applying a sequence of equally spaced pulses, and wherein the applying first and second sequences of magnetic field pulses comprises applying a sequence of magnetic field pulses having a power spectrum with an energy distribution across a range of frequencies in a series of closely spaced sticks;

capturing a magnetization spectrum resulting from each of the sequences of pulses; and analyzing a change in the magnetization spectrum resulting from the first and second sequences of pulses to extract information about the fluid.

11. The method of claim 10, wherein for each of the first and second sequences of pulses:

the pulses comprise a pulse width $\tau$; a flip angle $\alpha$, and a pulse spacing TE, with respect to time;

the closely spaced sticks of the energy distribution comprise a stick spacing 1/TE with respect to frequency; and the power spectrum comprises a central peak having a width $2/\tau$ with respect to frequency.

12. The method of claim 11, wherein:

the flip angle $\alpha$ and the pulse spacing TE for the second sequence of pulses are different from the flip angle $\alpha$ and the pulse spacing TE for the first sequence of pulses.

13. The method of claim 10, wherein the applying first and second sequences of magnetic field pulses comprises:

magnetically exciting the region at substantially only the frequencies of the sticks of the energy distribution of the applied sequence of pulses.

14. The method of claim 13, wherein the applying first and second sequences of magnetic field pulses comprises:

applying a sequence of magnetic field pulses configured to saturate the magnetization of the region where the region consists essentially of water.

15. The method of claim 10, wherein the analyzing comprises:

comparing the stick spectra of a captured magnetization spectrum with the stick spectra of the power spectrum.

16. The method of claim 14, wherein the analyzing comprises:

comparing the stick spectra of a captured magnetization spectrum with the stick spectra of the power spectrum.

17. The method of claim 15, wherein the analyzing comprises:

correlating the presence of a magnetization signal at frequencies only in the neighborhood of the stick spectra of the magnetization spectrum with the absence of diffusion; and correlating the presence of a magnetization signal at frequencies between the stick spectra of the magnetization spectrum with the presence of diffusion.

18. The method of claim 7, wherein:

the first and second sequences of magnetic field pulses each comprise a Carr-Purcell-Meiboom-Gill (CPMG) sequence.

19. The method of claim 11, wherein the applying first and second sequences of magnetic field pulses comprises:

applying a sequence of magnetic field pulses having a pulse spacing TE according to the following equation:

$$TE^{3/2} \geq \frac{1}{\gamma G\sqrt{2D}},$$

where $\gamma$ represents a magnetogyric ratio, G represents a field gradient, and D represents a diffusion constant.

20. The method of claim 19, wherein $\gamma$ and D are values associated with water.

21. The method of claim 7, wherein:
the first and second sequences of magnetic filed pulses each have a pulse spacing TE; and
the analyzing comprises analyzing a change in signal amplitude of the magnetization spectrum from the first and second sequences of pulses as a function of pulse spacing TE.

22. The method of claim 21, wherein:
the pulse spacing TE is equal to or less than about 8 milliseconds.

23. A method of evaluating a characteristic of a fluid in a region, comprising:
applying a magnetic field gradient to the region;
applying first and second sequences of magnetic field pulses to the region, each of the sequences having a power spectrum with an energy distribution across a range of frequencies in a series of closely spaced sticks, the second sequence differing in pulse characteristic to the first sequence; and
analyzing a resultant magnetization spectrum to extract information relating to signal attenuation resulting from the characteristics of the fluid in the region, the analyzed magnetization spectrum being represented as a function of frequency.

24. The method of claim 23, wherein the analyzing the resultant magnetization spectrum further comprises:
analyzing the signal attenuation of the magnetization spectrum resulting from the first and second sequences of pulses in relation to a diffusion characteristic relating to the fluid.

25. The method of claim 23, wherein the applying first and second sequences of magnetic field pulses comprises:
magnetically exciting the region at substantially only the frequencies of the sticks of the energy distribution of the applied sequence of pulses; and
applying a sequence of magnetic field pulses configured to saturate the nuclei magnetization of water.

26. The method of claim 25, wherein the applying first and second sequences of magnetic field pulses comprises:
applying a sequence of magnetic field pulses having a pulse spacing TE according to the following equation:

$$TE^{3/2} \geq \frac{1}{\gamma G\sqrt{2D}},$$

where $\gamma$ represents a magnetogyric ratio, G represents a field gradient, and D represents a diffusion constant.

27. The method of claim 26, wherein $\gamma$ and D are values associated with water.

\* \* \* \* \*